US007630753B2

(12) United States Patent
Simon et al.

(10) Patent No.: US 7,630,753 B2
(45) Date of Patent: Dec. 8, 2009

(54) METHOD AND APPARATUS FOR PERSPECTIVE INVERSION

(75) Inventors: David A Simon, Boulder, CO (US); Greg Rutz, Boulder, CO (US); Monish Rajpal, Boulder, CO (US); Gordon Goodchild, Broomfield, CO (US); Michael Haas, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 532 days.

(21) Appl. No.: 11/188,972

(22) Filed: Jul. 25, 2005

(65) Prior Publication Data

US 2005/0273004 A1 Dec. 8, 2005

Related U.S. Application Data

(63) Continuation of application No. 10/087,288, filed on Feb. 28, 2002, now Pat. No. 6,947,786.

(51) Int. Cl.
*A61B 5/05* (2006.01)
(52) U.S. Cl. ........................................ 600/427; 600/424
(58) Field of Classification Search ................. 600/424, 600/427, 425, 407, 410, 411, 414, 426, 439, 600/437; 250/363.01, 363.04; 606/97, 98; 378/4, 21, 22, 23, 24, 25, 26, 27
See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |

(Continued)

FOREIGN PATENT DOCUMENTS

CA        964149        3/1975

(Continued)

OTHER PUBLICATIONS

Adams, L., Knepper, A., Kyrbus, W., Meyer-Ebrecht, D., Pfeifer, G., Ruger, R., Witte, M., Aide au Reperage Tridimensionel pour la Chirurgie de la Base du Crane, Innov. Tech. Biol. Med., vol. 13, No. 4, 1992, pp. 409-424.

(Continued)

*Primary Examiner*—Daniel L Robinson
(74) *Attorney, Agent, or Firm*—Harness, Dickey (57) ABSTRACT

A surgical instrument navigation system is disclosed that allows a surgeon to invert the three-dimensional perspective of the instrument to match their perspective of the actual instrument. A data processor is operable to generate a three-dimensional representation of a surgical instrument as it would visually appear from either of at least two different perspectives and to overlay the representation of the surgical instrument onto an image data of the patient. The image data and the representations can be displayed on a display.

19 Claims, 6 Drawing Sheets

U.S. PATENT DOCUMENTS

| | | |
|---|---|---|
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,582,995 A * | 4/1986 | Lim et al. .............. 250/363.07 |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,257 A * | 11/1986 | Brown ........................... 341/5 |
| 4,621,628 A | 11/1986 | Bludermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |

| | | | | | |
|---|---|---|---|---|---|
| 5,030,222 A | 7/1991 | Calandruccio et al. | 5,299,253 A | 3/1994 | Wessels |
| 5,031,203 A | 7/1991 | Trecha | 5,299,254 A | 3/1994 | Dancer et al. |
| 5,042,486 A | 8/1991 | Pfeiler et al. | 5,299,288 A | 3/1994 | Glassman et al. |
| 5,047,036 A | 9/1991 | Koutrouvelis | 5,300,080 A | 4/1994 | Clayman et al. |
| 5,050,608 A | 9/1991 | Watanabe et al. | 5,305,091 A | 4/1994 | Gelbart et al. |
| 5,054,492 A | 10/1991 | Scribner et al. | 5,305,203 A | 4/1994 | Raab |
| 5,057,095 A | 10/1991 | Fabian | 5,306,271 A | 4/1994 | Zinreich et al. |
| 5,059,789 A | 10/1991 | Salcudean | 5,307,072 A | 4/1994 | Jones, Jr. |
| 5,078,140 A | 1/1992 | Kwoh | 5,309,913 A | 5/1994 | Kormos et al. |
| 5,079,699 A | 1/1992 | Tuy et al. | 5,315,630 A | 5/1994 | Sturm et al. |
| 5,086,401 A | 2/1992 | Glassman et al. | 5,316,024 A | 5/1994 | Hirschi et al. |
| 5,094,241 A | 3/1992 | Allen | 5,318,025 A | 6/1994 | Dumoulin et al. |
| 5,097,839 A | 3/1992 | Allen | 5,320,111 A | 6/1994 | Livingston |
| 5,098,426 A | 3/1992 | Sklar et al. | 5,325,728 A | 7/1994 | Zimmerman et al. |
| 5,099,845 A | 3/1992 | Besz et al. | 5,325,873 A | 7/1994 | Hirschi et al. |
| 5,099,846 A | 3/1992 | Hardy | 5,329,944 A | 7/1994 | Fabian et al. |
| 5,105,829 A | 4/1992 | Fabian et al. | 5,330,485 A | 7/1994 | Clayman et al. |
| 5,107,839 A | 4/1992 | Houdek et al. | 5,333,168 A | 7/1994 | Fernandes et al. |
| 5,107,843 A | 4/1992 | Aarnio et al. | 5,353,795 A | 10/1994 | Souza et al. |
| 5,107,862 A | 4/1992 | Fabian et al. | 5,353,800 A | 10/1994 | Pohndorf et al. |
| 5,109,194 A | 4/1992 | Cantaloube | 5,353,807 A | 10/1994 | DeMarco |
| 5,119,817 A | 6/1992 | Allen | 5,359,417 A | 10/1994 | Müller et al. |
| 5,142,930 A | 9/1992 | Allen et al. | 5,368,030 A | 11/1994 | Zinreich et al. |
| 5,143,076 A | 9/1992 | Hardy et al. | 5,371,778 A | 12/1994 | Yanof et al. |
| 5,152,288 A | 10/1992 | Hoenig et al. | 5,375,596 A | 12/1994 | Twiss et al. |
| 5,160,337 A | 11/1992 | Cosman | 5,377,678 A | 1/1995 | Dumoulin et al. |
| 5,161,536 A | 11/1992 | Vilkomerson et al. | 5,383,454 A | 1/1995 | Bucholz |
| 5,178,164 A | 1/1993 | Allen | 5,385,146 A | 1/1995 | Goldreyer |
| 5,178,621 A | 1/1993 | Cook et al. | 5,385,148 A | 1/1995 | Lesh et al. |
| 5,186,174 A | 2/1993 | Schlondorff et al. | 5,386,828 A | 2/1995 | Owens et al. |
| 5,187,475 A | 2/1993 | Wagener et al. | 5,389,101 A | 2/1995 | Heilbrun et al. |
| 5,188,126 A | 2/1993 | Fabian et al. | 5,391,199 A | 2/1995 | Ben-Haim |
| 5,190,059 A | 3/1993 | Fabian et al. | 5,394,457 A | 2/1995 | Leibinger et al. |
| 5,193,106 A | 3/1993 | DeSena | 5,394,875 A | 3/1995 | Lewis et al. |
| 5,197,476 A | 3/1993 | Nowacki et al. | 5,397,329 A | 3/1995 | Allen |
| 5,197,965 A | 3/1993 | Cherry et al. | 5,398,684 A | 3/1995 | Hardy |
| 5,198,768 A | 3/1993 | Keren | 5,399,146 A | 3/1995 | Nowacki et al. |
| 5,198,877 A | 3/1993 | Schulz | 5,400,384 A | 3/1995 | Fernandes et al. |
| 5,202,670 A * | 4/1993 | Oha .......................... 345/671 | 5,402,801 A | 4/1995 | Taylor |
| 5,207,688 A | 5/1993 | Carol | 5,408,409 A | 4/1995 | Glassman et al. |
| 5,211,164 A | 5/1993 | Allen | 5,413,573 A | 5/1995 | Koivukangas |
| 5,211,165 A | 5/1993 | Dumoulin et al. | 5,417,210 A | 5/1995 | Funda et al. |
| 5,211,176 A | 5/1993 | Ishiguro et al. | 5,419,325 A | 5/1995 | Dumoulin et al. |
| 5,212,720 A | 5/1993 | Landi et al. | 5,423,334 A | 6/1995 | Jordan |
| 5,214,615 A | 5/1993 | Bauer | 5,425,367 A | 6/1995 | Shapiro et al. |
| 5,219,351 A | 6/1993 | Teubner et al. | 5,425,382 A | 6/1995 | Golden et al. |
| 5,222,499 A | 6/1993 | Allen et al. | 5,426,683 A | 6/1995 | O'Farrell, Jr. et al. |
| 5,224,049 A | 6/1993 | Mushabac | 5,426,687 A | 6/1995 | Goodall et al. |
| 5,228,442 A | 7/1993 | Imran | 5,427,097 A | 6/1995 | Depp |
| 5,230,338 A | 7/1993 | Allen et al. | 5,429,132 A | 7/1995 | Guy et al. |
| 5,230,623 A | 7/1993 | Guthrie et al. | 5,433,198 A | 7/1995 | Desai |
| 5,233,990 A | 8/1993 | Barnea | RE35,025 E | 8/1995 | Anderton |
| 5,237,996 A | 8/1993 | Waldman et al. | 5,437,277 A | 8/1995 | Dumoulin et al. |
| 5,249,581 A | 10/1993 | Horbal et al. | 5,443,066 A | 8/1995 | Dumoulin et al. |
| 5,251,127 A | 10/1993 | Raab | 5,443,489 A | 8/1995 | Ben-Haim |
| 5,251,635 A | 10/1993 | Dumoulin et al. | 5,444,756 A | 8/1995 | Pai et al. |
| 5,253,647 A | 10/1993 | Takahashi et al. | 5,445,144 A | 8/1995 | Wodicka et al. |
| 5,255,680 A | 10/1993 | Darrow et al. | 5,445,150 A | 8/1995 | Dumoulin et al. |
| 5,257,636 A | 11/1993 | White | 5,445,166 A | 8/1995 | Taylor |
| 5,257,998 A | 11/1993 | Ota et al. | 5,446,548 A | 8/1995 | Gerig et al. |
| 5,261,404 A | 11/1993 | Mick et al. | 5,446,799 A * | 8/1995 | Tuy .......................... 382/132 |
| 5,265,610 A | 11/1993 | Darrow et al. | 5,447,154 A | 9/1995 | Cinquin et al. |
| 5,265,611 A | 11/1993 | Hoenig et al. | 5,448,610 A | 9/1995 | Yamamoto et al. |
| 5,269,759 A | 12/1993 | Hernandez et al. | 5,453,686 A | 9/1995 | Anderson |
| 5,271,400 A | 12/1993 | Dumoulin et al. | 5,456,718 A | 10/1995 | Szymaitis |
| 5,273,025 A | 12/1993 | Sakiyama et al. | 5,457,641 A | 10/1995 | Zimmer et al. |
| 5,274,551 A | 12/1993 | Corby, Jr. | 5,458,718 A | 10/1995 | Venkitachalam |
| 5,279,309 A | 1/1994 | Taylor et al. | 5,464,446 A | 11/1995 | Dreessen et al. |
| 5,285,787 A | 2/1994 | Machida | 5,469,847 A | 11/1995 | Zinreich et al. |
| 5,291,199 A | 3/1994 | Overman et al. | 5,478,341 A | 12/1995 | Cook et al. |
| 5,291,889 A | 3/1994 | Kenet et al. | 5,478,343 A | 12/1995 | Ritter |
| 5,295,483 A | 3/1994 | Nowacki et al. | 5,480,422 A | 1/1996 | Ben-Haim |
| 5,297,549 A | 3/1994 | Beatty et al. | 5,480,439 A | 1/1996 | Bisek et al. |

| Patent | Date | Inventor |
|---|---|---|
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-Haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Taylor et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,913,820 A | 6/1999 | Bladen et al. |
| 5,920,395 A | 7/1999 | Schulz |

| | | | |
|---|---|---|---|
| 5,921,992 A | 7/1999 | Costales et al. | |
| 5,923,727 A | 7/1999 | Navab | |
| 5,928,248 A | 7/1999 | Acker | |
| 5,938,603 A | 8/1999 | Ponzi | |
| 5,938,694 A | 8/1999 | Jaraczewski et al. | |
| 5,947,980 A | 9/1999 | Jensen et al. | |
| 5,947,981 A | 9/1999 | Cosman | |
| 5,950,629 A | 9/1999 | Taylor et al. | |
| 5,951,475 A | 9/1999 | Gueziec et al. | |
| 5,951,571 A | 9/1999 | Audette | |
| 5,954,647 A | 9/1999 | Bova et al. | |
| 5,957,844 A | 9/1999 | Dekel et al. | |
| 5,964,796 A | 10/1999 | Imran | |
| 5,967,980 A | 10/1999 | Ferre et al. | |
| 5,967,982 A | 10/1999 | Barnett | |
| 5,968,047 A | 10/1999 | Reed | |
| 5,971,997 A | 10/1999 | Guthrie et al. | |
| 5,976,156 A | 11/1999 | Taylor et al. | |
| 5,980,535 A | 11/1999 | Barnett et al. | |
| 5,983,126 A | 11/1999 | Wittkampf | |
| 5,987,349 A | 11/1999 | Schulz | |
| 5,987,960 A | 11/1999 | Messner et al. | |
| 5,999,837 A | 12/1999 | Messner et al. | |
| 5,999,840 A | 12/1999 | Grimson et al. | |
| 6,001,130 A | 12/1999 | Bryan et al. | |
| 6,006,126 A | 12/1999 | Cosman | |
| 6,006,127 A | 12/1999 | Van Der Brug et al. | |
| 6,013,087 A | 1/2000 | Adams et al. | |
| 6,014,580 A | 1/2000 | Blume et al. | |
| 6,016,439 A | 1/2000 | Acker | |
| 6,019,725 A | 2/2000 | Vesely et al. | |
| 6,024,695 A | 2/2000 | Greenberg et al. | |
| 6,050,724 A | 4/2000 | Schmitz et al. | |
| 6,059,718 A | 5/2000 | Taniguchi et al. | |
| 6,063,022 A | 5/2000 | Ben-Haim | |
| 6,071,288 A | 6/2000 | Carol et al. | |
| 6,073,043 A | 6/2000 | Schneider | |
| 6,076,008 A | 6/2000 | Bucholz | |
| 6,096,050 A | 8/2000 | Audette | |
| 6,104,944 A | 8/2000 | Martinelli | |
| 6,118,845 A | 9/2000 | Simon et al. | |
| 6,122,538 A | 9/2000 | Sliwa, Jr. et al. | |
| 6,122,541 A | 9/2000 | Cosman et al. | |
| 6,131,396 A | 10/2000 | Duerr et al. | |
| 6,139,183 A | 10/2000 | Graumann | |
| 6,147,480 A | 11/2000 | Osadchy et al. | |
| 6,149,592 A | 11/2000 | Yanof et al. | |
| 6,156,067 A | 12/2000 | Bryan et al. | |
| 6,161,032 A | 12/2000 | Acker | |
| 6,165,181 A | 12/2000 | Heilbrun et al. | |
| 6,167,296 A | 12/2000 | Shahidi | |
| 6,172,499 B1 | 1/2001 | Ashe | |
| 6,175,756 B1 | 1/2001 | Ferre et al. | |
| 6,178,345 B1 | 1/2001 | Vilsmeier et al. | |
| 6,194,639 B1 | 2/2001 | Botella et al. | |
| 6,201,387 B1 | 3/2001 | Govari | |
| 6,203,497 B1 | 3/2001 | Dekel et al. | |
| 6,211,666 B1 | 4/2001 | Acker | |
| 6,223,067 B1 | 4/2001 | Vilsmeier | |
| 6,233,476 B1 | 5/2001 | Strommer et al. | |
| 6,246,231 B1 | 6/2001 | Ashe | |
| 6,259,942 B1 | 7/2001 | Westermann et al. | |
| 6,273,896 B1 | 8/2001 | Franck et al. | |
| 6,285,902 B1 | 9/2001 | Kienzle, III et al. | |
| 6,298,262 B1 | 10/2001 | Franck et al. | |
| 6,314,310 B1 | 11/2001 | Ben-Haim et al. | |
| 6,332,089 B1 | 12/2001 | Acker et al. | |
| 6,341,231 B1 | 1/2002 | Ferre et al. | |
| 6,351,659 B1 | 2/2002 | Vilsmeier | |
| 6,381,485 B1 | 4/2002 | Hunter et al. | |
| 6,424,856 B1 | 7/2002 | Vilsmeier et al. | |
| 6,427,314 B1 | 8/2002 | Acker | |
| 6,428,547 B1 | 8/2002 | Vilsmeier et al. | |
| 6,434,415 B1 | 8/2002 | Foley et al. | |
| 6,437,567 B1 | 8/2002 | Schenck et al. | |
| 6,445,943 B1 | 9/2002 | Ferre et al. | |
| 6,470,207 B1 | 10/2002 | Simon et al. | |
| 6,474,341 B1 | 11/2002 | Hunter et al. | |
| 6,477,226 B1 * | 11/2002 | Lehmann et al. ............... 378/44 |
| 6,477,228 B2 | 11/2002 | Spahn | |
| 6,478,802 B2 | 11/2002 | Kienzle, III et al. | |
| 6,484,049 B1 | 11/2002 | Seeley et al. | |
| 6,490,475 B1 | 12/2002 | Seeley et al. | |
| 6,493,573 B1 | 12/2002 | Martinelli et al. | |
| 6,493,575 B1 * | 12/2002 | Kesten et al. ............... 600/431 |
| 6,498,944 B1 | 12/2002 | Ben-Haim et al. | |
| 6,499,488 B1 | 12/2002 | Hunter et al. | |
| 6,516,046 B1 | 2/2003 | Fröhlich et al. | |
| 6,527,443 B1 | 3/2003 | Vilsmeier et al. | |
| 6,529,758 B2 * | 3/2003 | Shahidi ...................... 600/407 |
| 6,551,325 B2 | 4/2003 | Neubauer et al. | |
| 6,567,690 B2 * | 5/2003 | Giller et al. ................. 600/473 |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,694,162 B2 | 2/2004 | Hartlep | |
| 6,695,786 B2 * | 2/2004 | Wang et al. ................. 600/461 |
| 6,701,179 B1 | 3/2004 | Martinelli et al. | |
| 2001/0007918 A1 | 7/2001 | Vilsmeier et al. | |
| 2002/0095081 A1 | 7/2002 | Vilsmeier | |
| 2004/0024309 A1 | 2/2004 | Ferre et al. | |

FOREIGN PATENT DOCUMENTS

| | | |
|---|---|---|
| DE | 3042343 | 6/1982 |
| DE | 35 08730 | 3/1985 |
| DE | 37 17 871 | 5/1987 |
| DE | 38 38011 | 11/1988 |
| DE | 3831278 A1 | 3/1989 |
| DE | 42 13 426 | 4/1992 |
| DE | 42 25 112 | 7/1992 |
| DE | 4233978 C1 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 10085137 | 11/2002 |
| EP | 0 062 941 | 3/1982 |
| EP | 0 119 660 | 9/1984 |
| EP | 0 155 857 | 1/1985 |
| EP | 0 319 844 A1 | 1/1988 |
| EP | 0 326 768 | 12/1988 |
| EP | 0 419 729 A1 | 9/1989 |
| EP | 350 996 | 1/1990 |
| EP | 0 651 968 A1 | 8/1990 |
| EP | 0 427 358 | 10/1990 |
| EP | 0 456 103 | 5/1991 |
| EP | 0 581 704 A1 | 7/1993 |
| EP | 0 655 138 B1 | 8/1993 |
| EP | 0 894 473 A2 | 1/1995 |
| EP | 0 908 146 | 10/1998 |
| EP | 0 930 046 | 10/1998 |
| FR | 2 417 970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 4/1991 |
| WO | WO 88/09151 | 12/1988 |
| WO | WO 89/05123 | 6/1989 |
| WO | WO 90/05494 | 5/1990 |
| WO | WO 91/03982 | 4/1991 |

| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/36192 | 10/1997 |
| WO | WO 97/49453 | 12/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO 01/30437 A1 | 5/2001 |

OTHER PUBLICATIONS

Ali Hamadeh et al., "Automated 3-Dimensional Computer Tomographic and Fluorscopic Image Registration," Computer Aided Surgery (1998), 3:11-19.

Ali Hamadeh et al., "Towards Automatic Registration Between CT and X-ray Images: Cooperation Between 3D/2D Registration and 2D Edge Detection," MRCAS '95, pp. 39-46.

Andre P. Gueziec et al., "Registration of Computer Tomography Data to a Surgical Robot Using Fluorscopy: A Feasibility Study," Computer Science/Mathematics, Sep. 27, 1996, 6 pages.

Barrick, Frederick E., et al., "Phophylactic Intramedullary Fixation of the Tibia for Stress Fracture in a Professional Athlete," Journal of Orthopaedic Trauma, vol. 6, No. 2, pp. 241-244 (1992).

Barrick, Frederick E., et al., "Technical Difficulties with the Brooker-Wills Nail in Acute Fractures of the Femur," Journal of Orthopaedic Trauma, vol. 6, No. 2, pp. 144-150 (1990).

Batnitzky, S., Price, H.I., Lee, K.R., Cook, P.N., Cook, L.T., Fritz, S.L., Dwyer, S.J., Watts, C., Three-Dimensinal Computer Reconstructions of Brain Lesions from Surface Contours Provided by Computed Tomography: A Prospectus, Neurosurgery, vol. 11, No. 1, Part 1, 1982, pp. 73-84.

Bouazza-Marouf et al.; "Robotic-Assisted Internal Fixation of Femoral Fractures", IMECHE.pp. 51-58 (1995).

C. Brack et al., "Accurate X-ray Based Navigation in Computer-Assisted Orthopedic Surgery," CAR '98, pp. 716-722.

Champleboux, G., Utilisation de Fonctions Splines pour la Mise au Point D'un Capteur Tridimensionnel sans Contact, Quelques Applications Medicales, Jul. 1991.

Cinquin, P., Lavallee, S., Demongeot, J., Computer Assisted Medical Interventions, International Advanced Robotics Programme, Sep. 1989, pp. 63-65.

Clarysse, P., Gibon, D., Rousseau, J., Blond, S., Vasseur, C., Marchandise, X., A Computer-Assisted System for 3-D Frameless Localization in Stereotaxic MRI, IEEE Transactions on Medical Imaging, vol. 10, No. 4, Dec. 1991, pp. 523-529.

Colchester, A.C.F., Hawkes, D.J., Information Processing in Medical Imaging, Lecture Notes in Computer Science, 12th International Conference, IPMI, Jul. 1991, pp. 136-141.

E. Frederick Barrick, "Journal of Orthopaedic Trauma: Distal Locking Screw Insertion Using a Cannulated Drill Bit: Technical Note," Raven Pres, vol. 7, No. 3, 1993, pp. 248-251.

Foley, J.D., Van Dam, A., Fundamentals of Interactive Computer Graphics, The Systems Programming Series, Chapter 7, Jul. 1984, pp. 245-266.

Foley, K.T., Smith, K.R., Bucholz, R.D., Image-guided intraoperative Spinal Localization, Intraoperative Neuroprotection, Chapter 19, 1996, pp. 325-340.

Foley, K.T., The SteathStation. Three-Dimensional Image-Interactive Guidance for the Spine Surgeon, Spinal Frontiers, Apr. 1996, pp. 7-9.

G. Selvik, et al., "A Roentgen Stereophotogrammetric System," Acta Radiologica Diagnosis, 1983, pp. 343-352.

Gildenberg, P.L., Kaufman, H.H. Murthy, K.S., Calculation of Stereotactic Coordinates from the Computed Tomographic Scan, Neurosurgery, vol. 10, No. 5, May 1982, pp. 580-586.

Gonzalez, R.C., Digital Image Fundamentals, Digital Image Processing, Second Edition, 1987, pp. 52-54.

Hatch, J.F., Reference-Display System for the Integration of CT Scanning and the Operating Microscope, Thesis, Thayer School of Engineering, Oct. 1984, pp. 1-189.

Henderson, J.M., Smith, K.R. Bucholz, R.D., An Accurate and Ergonomic Method of Registration for Image-guided Neurosurgery, Computerized Medical Imaging and Graphics, vol. 18, No. 4, Jul.-Aug. 1994, pp. 273-277.

Hoerenz, P., The Operating Microscope I. Optical Principles, Illumination Systems, and Support Systems, Journal of Microsurgery, vol. 1, 1980, pp. 364-369.

Hounsfield, G.N., Computerized transverse axial scanning (tomography): Part 1. Description of system, British Journal of Radiology, vol. 46, No. 552, Dec. 1973, pp. 1016-1022.

Jacques Feldmar et al., "3D-2D Projective Registration of Free-Form Curves and Surfaces," Rapport de recherche (Inria Sophia Antipolis), 1994, pp. 1-44.

Jacques, S., Sheldon, C.H., McCann, G.D., A Computerized Microstereotactic Method to Approach, 3-Dimensionally Reconstruct, Remove and Adjuvantly Treat Small CNS Lesions, Applied Neurophysiology, vol. 43, 1980, pp. 176-182.

Jacques, S., Sheldon, C.H., McCann, G.D., Freshwater, D.B., Rand, R., Computerized three-dimensional stereotaxic removal of small central nervous system lesion in patients, J. Neurosurg., vol. 53, Dec. 1980, pp. 816-820.

Jurgen Weese, et al., "An Approach to 2D/3D Registration of a Vertebra in 2D X-ray Fluoroscopies with 3D CT Images," pp. 119-128.

Kelly, P.J., Kall, B., Goerss, S., Alker, G.J., Jr., Precision Resection of Intra-Axial CNS Lesions by CT-Based Stereotactic Craniotomy and Computer Monitored CO Laser, Acta Neurochirurgica, vol. 68, 1983, pp. 1-9.

L. Lemieux et al., "A Patient-to-Computer-Tomography Image Registration Method Based on Digitally Reconstructed Radiographs," Med. Phys. 21 (11), Nov. 1994, pp. 1749-1760.

Lavallee, S., A New System for Computer Assisted Neurosurgery, IEEE Engineering in Medicine & Biology Society 11th Annual International Conference, 1989, pp. 0926-0927.

Lavallee, S., Brunie, L., Mazier, B., Cinquin, P., Matching of Medical Images for Computed and Robot Assisted Surgery, IEEE EMBS, Orlando, 1991.

Lavallee, S., Cinquin, P., Dermongeot, J., Benabid, A.L., Marque, I., Djaid M.,Computer Assisted Interventionist Imaging: The Instance of Stereotactic Brain Surgery, North-Holland MEDINFO 89, Part 1, 1989, pp. 613-617.

Lavallee, S., Cinquin, P., Dermongeot, J., Benabid, A.L., Marque, I., Djaid, M., Computer Assisted Driving of a Needle into the Brain, Proceedings of the International Symposium CAR '89, Computer Assisted Radiology, 1989, pp. 416-420.

Lavallee, S., VI Adaption de la Methodologie a Quelques Applications Cliniques, Chapitre VI, pp. 133-148.

Lavallee, S., Zseliski, R., Brunie, L., Matching 3-D Smooth Surfaces with Their 2-D Projections using 3-D Distance Maps, SPIE, vol. 1570, Geometric Methods in Computer Vision, 1991, pp. 322-336.

Leksell, L., Jernberg, B. Stereotaxis and Tomography—A Technical Note, ACTA Neurochirurgica, vol. 52, 1980, pp. 1-7.

Leo Joskowicz et al., "Computer-Aided Image-Guided Bone Fracture Surgery: Concept and Implementation," CAR '98, pp. 710-715.

Levin, D.N., Hu, X., Tan, K.K., Galhotra, S., Pelizzari, C.A., Chen, G.T.Y., Beck, R.N., Chen. C., Cooper, M.D., Mullan, J.F., Hekmatpanah, J., Spire, J., The Brain: Integrated Three-dimensional Display of MR and PET Images, Radiology, vol. 172, No. 3, Sep. 1989, pp. 783-789.

Lisa M. Gottesfeld Brown et al., "Registration of Planar Film Radiographs with Computer Tomography," Proceedings of MMBIA, Jne '96, pp. 42-51.

Mazier, B., Lavallee, S., Cinquin, P., Chirurgie de la Colonne Vertebrale Assistee par Ordinateur: Appication au Vissage Pediculaire, Innov. Tech. Biol. Med., vol. 11, No. 5, 1990, pp. 559-566.

Mazier, B., Lavallee, S., Cinquin, P., Computer-Assisted Interventionist Imaging: Application to the Vertebral Column Surgery, Annual International Conference of the IEEE Engineering in Medicine and Biology Society, vol. 12, No. 1, 1990, pp. 0430-0431.

P. Cinquin, et al, "Kinematic Study of Lumbar Spine Using Functional Radiographies and 3D/2D Registration," TIMC UMR 5525—IMAG.

P. Cinquin, et al., "Computer Assisted Medical Interventions," IEEE Engineering in Medicine and Biology, May/Jun. 1995, pp. 254-263.

P. Cinquin, et al., "Computer Assisted Spine Surgery: A Technique For Accurate Transpedicular Screw Fixation Using CT Data and a 3-D Optical Localizer," TIMC, Faculte de Medecine de Grenoble.

P. Potamianos, et al., "Intra-Operative Imaging Guidance for Keyhole Surgery Mehtodology and Calibration," First International Symposium on Medical Robotics and Computer Assisted Surgery, Sep. 22-24, 1994, pp. 98-104.

Pascal Phillipe Sautot, "Vissage Pediculaire Assiste Par Ordinateur," Sep. 20, 1994.

Pelizzari, C.A., Chen, G.T.Y., Halpern, H., Chen, C.T., Cooper, M.D., No. 528—Three Dimensional Correlation of PET, CT and MRI Images, The Journal of Nuclear Medicine, vol. 28, No. 4, Apr. 1987, p. 682.

Pelizzari, C.A., Chen, G.T.Y., Spelbring, D.R., Weichselbaum, R.R., Chen, C., Accurate Three-Dimensional Registration of CT, PET, and/or MR Images of the Brain, Journal of Computer Assisted Tomography, Jan./Feb. 1989, pp. 20-26.

R. Hofstetter et al., "Fluoroscopy Based Surgical Navigation—Concept and Clinical Applications," Computer Assisted Radiology and Surgery, 1997, pp. 956-960.

R. Phillips et al., "Image Guided Orthopaedic Surgery Design and Analysis," Trans Inst. MC, vol. 17, No. 5, 1995, pp. 251-264.

Reinhardt, H.F., Landolt, H., CT-Guided "Real Time" Stereotaxy, ACTA Neurochirurgica, 1989.

Roberts, D.W., Strohbehn, J.W., Hatch, J.F. Murray, W. Kettenberger, H., A frameless stereotaxic integration of computerized tomographic imaging and the operating microscope, J. Neurosurg., vol. 65, Oct. 1986, pp. 545-549.

Rosenbaum, A.E., Lunsford, L.D., Perry, J.H., Computerized Tomography Guided Stereotaxis: A New Approach, Applied Neurophysiology, vol. 43, No. 3-5, 1980, pp. 172-173.

Sheldon, C.H., McCann, G., Jacques, S., Lutes, H.R., Frazier, R.E., Katz, R., Kuki, R., Development of a computerized microsteroetaxic method for localization and removal of minute CNS lesions under direct 3-D vision, J. Neurosurg., vol. 52, 1980, pp. 21-27.

Smith, K.R., Bucholz, R.D., Computer Methods for Improved Diagnostic Image Display Applied to Stereotactic Neurosurgery, Automedical, vol. 14, 1992, pp. 371-382.

Stephane Lavallee, et al., "Image guided operating robot: a clinical application in stereotactic neurosurgery," Proceedings of the 1992 IEEE Internation Conference on Robotics and Automation, May 1992,pp. 618-624.

W.J. Viant et al., "A Computer Assisted Orthopaedic System for Distal Locking of Intramedullary Nails," Proc. MediMEC '95, Bristol, 1995, pp. 86-91.

Watanabe, E., Watanabe, T., Manaka, S., Mayanagi, Y., Takakura, K., Three-Dimensional Digitizer (Neuronavigator): New Equipment for Computed Tomography-Guided Stereotaxic Surgery, Surgical Neurology, vol. 27, No. 6, Jun. 1987, pp. 543-547.

Watanabe, H., Neuronavigator, Igaku-no-Ayumi, vol. 137, No. 6, May 10, 1986, pp. 1-4.

"Prestige Cervical Disc System Surgical Technique", 12 pgs.

Benzel et al., "Magnetic Source Imaging: a Review of the Magnes System of Biomagnetic Technologies Incorporated," Neurosurgery, vol. 33, No. 2 (Aug. 1993), pp. 252-259.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May 1992.

Feldmar et al., "3D-2D Projective Registration of Free-Form Curves and Surfaces," Rapport de recherche (Inria Sophia Antipolis), 1994, pp. 1-44.

Hamadeh et al, "Kinematic Study of Lumbar Spine Using Functional Radiographies and 3D/2D Registration," TIMC UMR 5525—IMAG.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Kelly et al., "Computer-assisted stereotaxic laser resection of intraaxial brain neoplasms," Journal of Neurosurgery, vol. 64, Mar. 1986, pp. 427-439.

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Reinhardt et al., "CT-Guided 'Real Time' Stereotaxy," ACTA Neurochirurgica, 1989.

Schueler et al., "Correction of Image Intensifier Distortion for Three-Dimensional X-Ray Angiography," SPIE Medical Imaging 1995, vol. 2432, pp. 272-279.

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.

Germano, "Instrumentation, Technique and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, May 1985, pp. 252-254.

Adams et al., Computer-Assisted Surgery, IEEE Computer Graphics & Applications, pp. 43-51, (May 1990).

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., Jr. et al, Optical localization for interactive, image-guided neurosurgery, SPIE, vol. 2164, pp. 137-145 (undated.

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Guthrie, B.L., Graphic-Interactive Cranial Surgery: The Operating Arm System, Handbook of Stereotaxy Using the CRW Apparatus, Chapter 13, pp. 193-211 (undated.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Computer-Directed Stereotactic Resection of Brain Tumors, Neurologica Operative Atlas, vol. 1, No. 4, pp. 299-313 (1991).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep. -Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. and Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

* cited by examiner

METHOD AND APPARATUS FOR PERSPECTIVE INVERSION

CROSS-REFERENCE TO RELATED APPLICATIONS

This application is a continuation of U.S. patent application Ser. No. 10/087,288 filed on Feb. 28, 2002. The disclosure of the above application is incorporated herein by reference.

FIELD

The present teachings relate generally to surgical instrument navigation systems and, more particularly, to a navigation system that provides perspective inversion of the surgical instrument.

BACKGROUND

Modern diagnostic medicine has benefited significantly from radiology. Radiation, such as x-rays, may be used to generate images of internal body structures. In general, radiation is emanated towards a patient's body and absorbed in varying amounts by tissues in the body. An x-ray image is then created based on the relative differences of detected radiation passing through the patients' body.

Surgical navigation guidance can provide a tool for helping the physician perform surgery. One known technique involves tracking position in real-time of a surgical instrument in the patient's anatomy as it is represented by an x-ray image. The virtual representation of the surgical instrument is a three-dimensional object superimposed onto the two-dimensional image of the patient. Thus, the three-dimensional representation appears to be directed into or out of the two-dimensional image of the patient. An exemplary surgical navigation guidance system is disclosed in U.S. application Ser. No. 09/274,972 filed on Mar. 23, 1999 which is assigned to the assignee of the present teachings and incorporated herein by reference.

When an image is acquired, it is acquired from a certain perspective or point-of-view. In the case of a C-arm imaging device, the perspective is determined by the orientation of the C-arm around the patient. Specifically, the perspective is along the line connecting the image source and the image receiver. If the surgeon navigates the surgical instrument from the position of the image receiver, the perspective of the virtual representation of the instrument will match the surgeon's perspective of the actual instrument. However, if the surgeon navigates from the position of the radiation source, the perspective of the virtual representation of the instrument will appear "flipped" from the surgeon's perspective of the actual instrument.

Therefore, it is desirable to provide a surgical navigation system that allows the surgeon to invert or "flip" the three-dimensional perspective of the instrument to match their perspective of the actual instrument.

SUMMARY

In accordance with the present teachings, a surgical instrument navigation system is provided that allows a surgeon to invert the three-dimensional perspective of the instrument to match their perspective of the actual instrument. The surgical instrument navigation system includes: a surgical instrument; an imaging device that is operable to capture image data representative of a patient; a tracking subsystem that is operable to capture in real-time position data indicative of the position of the surgical instrument; and a data processor adapted to receive the image data from the imaging device and the position data from the tracking subsystem. The data processor is operable to generate a three-dimensional representation of the surgical instrument as it would visually appear from either of at least two different perspectives and to overlay the representation of the surgical instrument onto the image data of the patient. The navigation system further includes a display that is operable to display the representation of the surgical instrument superimposed onto the image data of the patient.

For a more complete understanding of the teachings, reference may be made to the following specification and to the accompanying drawings.

DETAILED DESCRIPTION OF THE VARIOUS EMBODIMENTS

Figure 1:
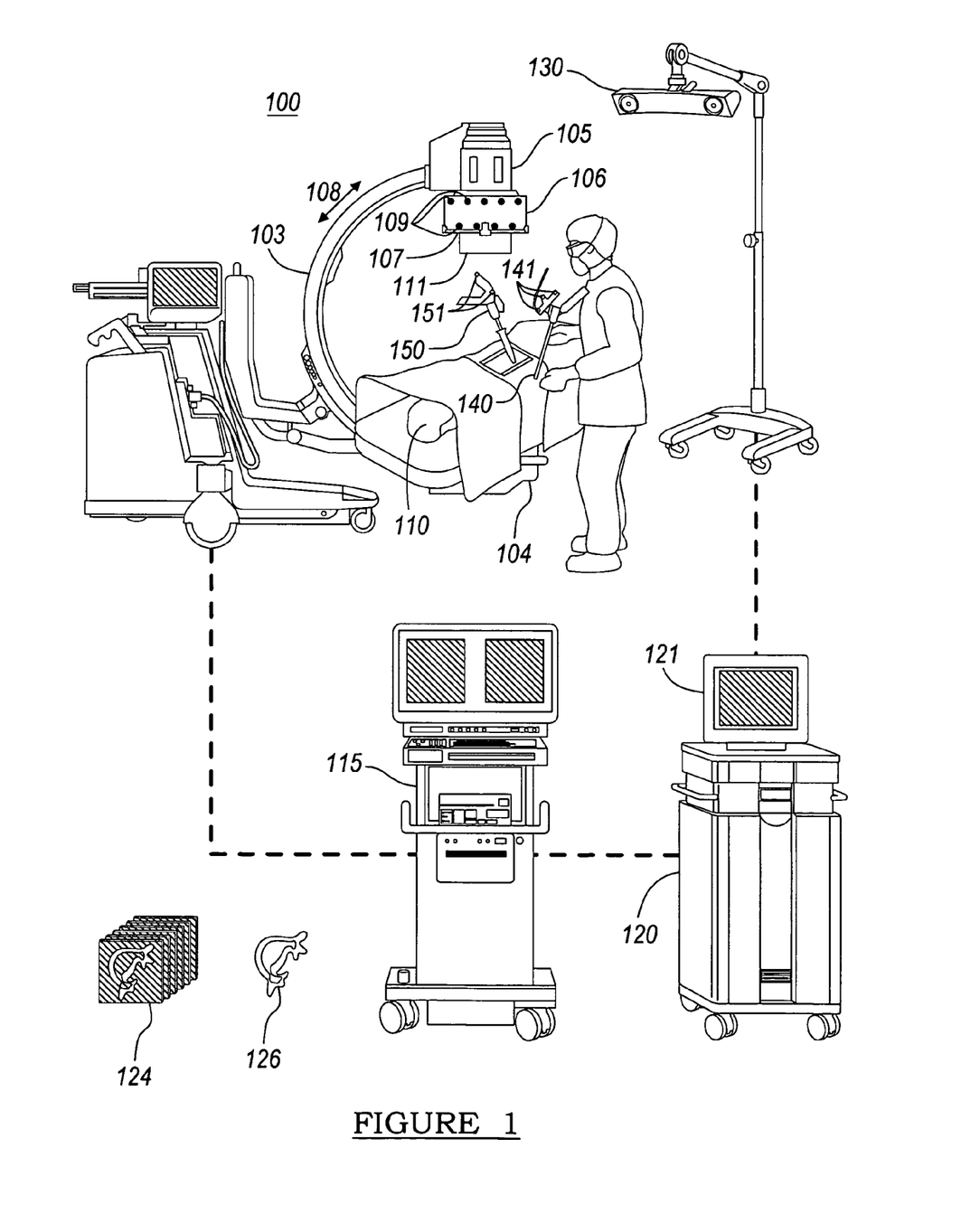
FIG. 1 is a diagram of a surgical instrument navigation system in accordance with present teachings.

FIG. 1 is a diagram of an exemplary surgical instrument navigation system. The primary component of the surgical instrument navigation system is a fluoroscopic imaging device 100. The fluoroscopic imaging device 100 generally includes a C-arm 103, x-ray source 104, x-ray receiving section 105, a calibration and tracking target 106, and radiation sensors 107. Calibration and tracking target 106 includes infrared reflectors (or alternatively infrared emitters) 109 and calibration markers 111. C-arm control computer 115 allows a physician to control the operation of imaging device 100, such as setting imaging parameters. One appropriate implementation of imaging device 100 is the "Series 9600 Mobile Digital Imaging System," from OEC Medical Systems, Inc., of Salt Lake City, Utah. It should be noted that calibration and tracking target 106 and radiation sensors 107 are typically not included in the Series 9600 Mobile Digital Imaging System; otherwise the "Series 9600 Mobile Digital Imaging System" is similar to imaging system 100.

In operation, x-ray source 104 generates x-rays that propagate through patient 110 and calibration target 106, and into x-ray receiving section 105. Receiving section 105 generates an image representing the intensities of the received x-rays. Typically, receiving section 105 comprises an image intensifier that converts the x-rays to visible light and a charge coupled device (CCD) video camera that converts the visible light to digital images. Receiving section 105 may also be a device that converts x-rays directly to digital images, thus potentially avoiding distortion introduced by first converting to visible light.

Fluoroscopic images taken by imaging device 100 are transmitted to computer 115, where they may further be forwarded to computer 120. Computer 120 provides facilities for displaying (on monitor 121), saving, digitally manipulating, or printing a hard copy of the received images. Three-dimensional images, such as pre-acquired patient specific CT/MR data set 124 or a three-dimensional atlas data set 126 may also be manipulated by computer 120 and displayed by monitor 121. Images, instead of or in addition to being displayed on monitor 121, may also be displayed to the physician through a heads-up-display.

Although computers 115 and 120 are shown as two separate computers, they alternatively could be variously implemented as multiple computers or as a single computer that performs the functions performed by computers 115 and 120. In this case, the single computer would receive input from both C-arm imager 100 and tracking sensor 130.

Radiation sensors 107 sense the presence of radiation, which is used to determine whether or not imaging device 100 is actively imaging. The result of their detection is transmitted to processing computer 120. Alternatively, a person may manually indicate when device 100 is actively imaging or this function can be built into x-ray source 104, x-ray receiving section 105, or control computer 115.

In operation, the patient is positioned between the x-ray source 104 and the x-ray receiving section 105. In response to an operator's command input at control computer 115, x-rays emanate from source 104 and pass through patient 110, calibration target 106, and into receiving section 105 which generates a two-dimensional image of the patient.

C-arm 103 is capable of rotating relative to patient 110, thereby allowing images of patient 110 to be taken from multiple directions. For example, the physician may rotate C-arm 103 in the direction of arrows 108 or about the long axis of the patient. Each of these directions of movement involves rotation about a mechanical axis of the C-arm. In this example, the long axis of the patient is aligned with the mechanical axis of the C-arm.

Figure 2A:
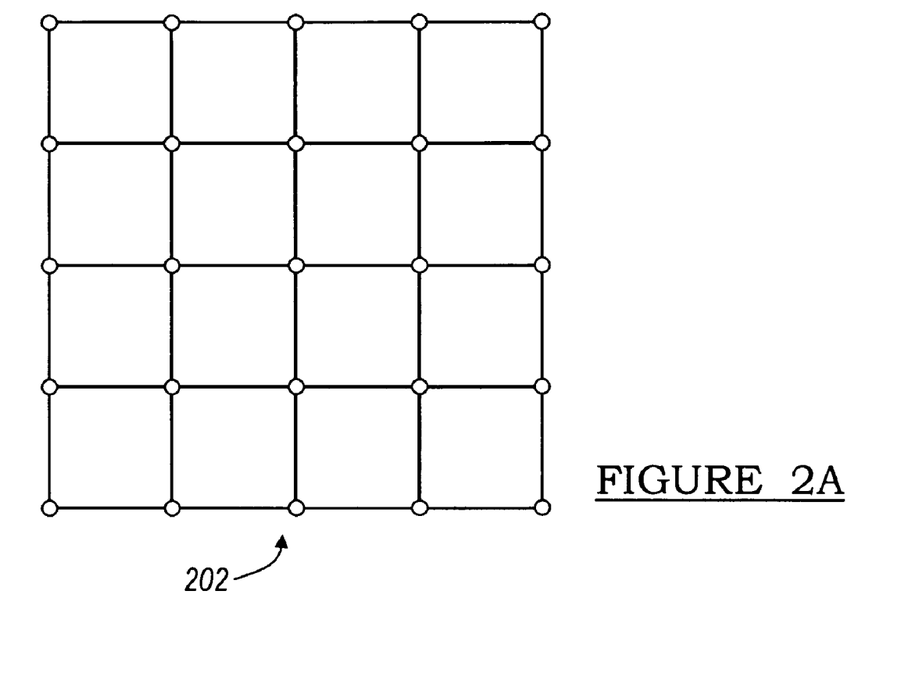
FIG. 2 is a diagram of an ideal and distorted image that may be captured by the surgical navigation system.
Figure 2B:
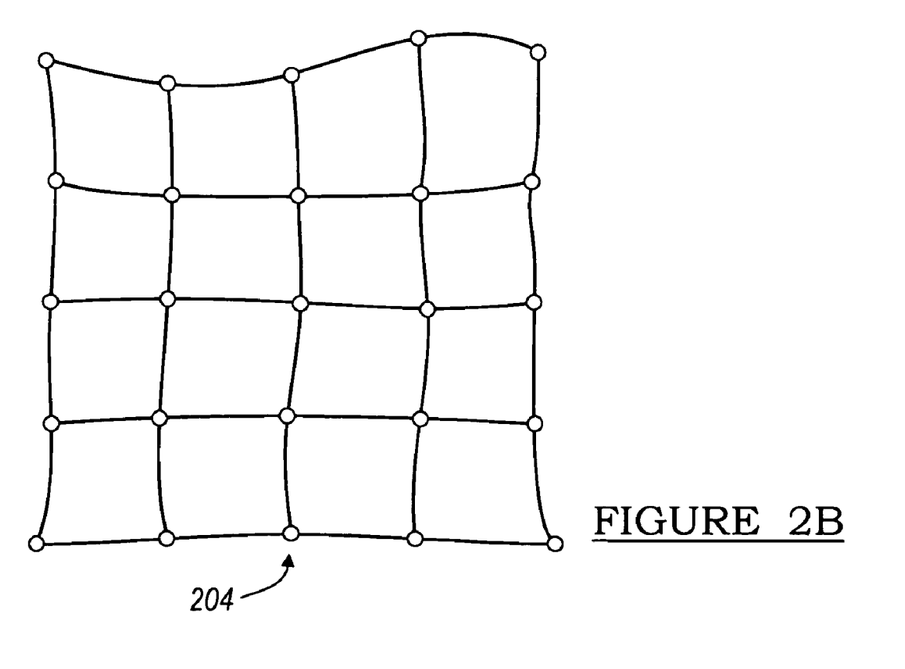

Raw images generated by receiving section 105 tend to suffer from undesirable distortion caused by a number of factors, including inherent image distortion in the image intensifier and external electromagnetic fields. Drawings representing ideal and distorted images are shown in FIG. 2. Checkerboard 202 represents the ideal image of a checkerboard shaped object. The image taken by receiving section 105, however, can suffer significant distortion, as illustrated by distorted image 204.

Figure 3A:
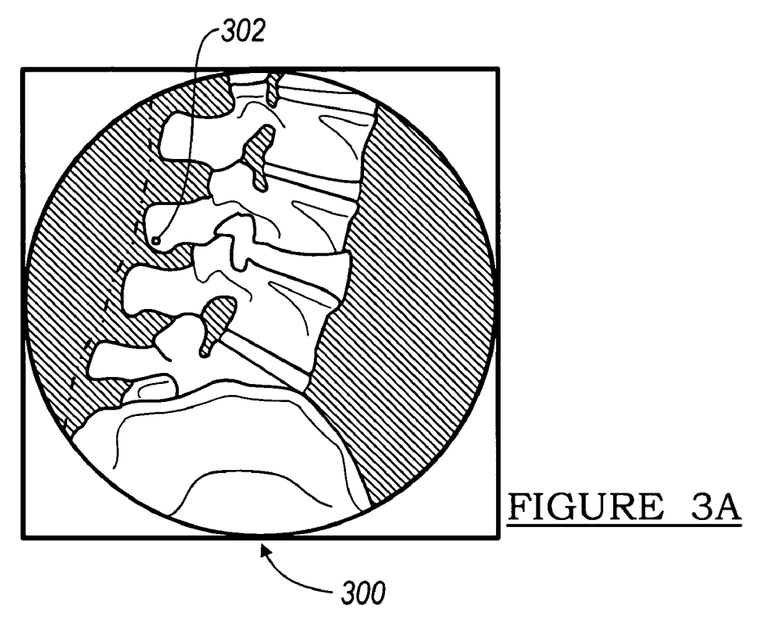
FIGS. 3A and 3B illustrates the projective transformation process employed by the surgical navigation system.
Figure 3B:
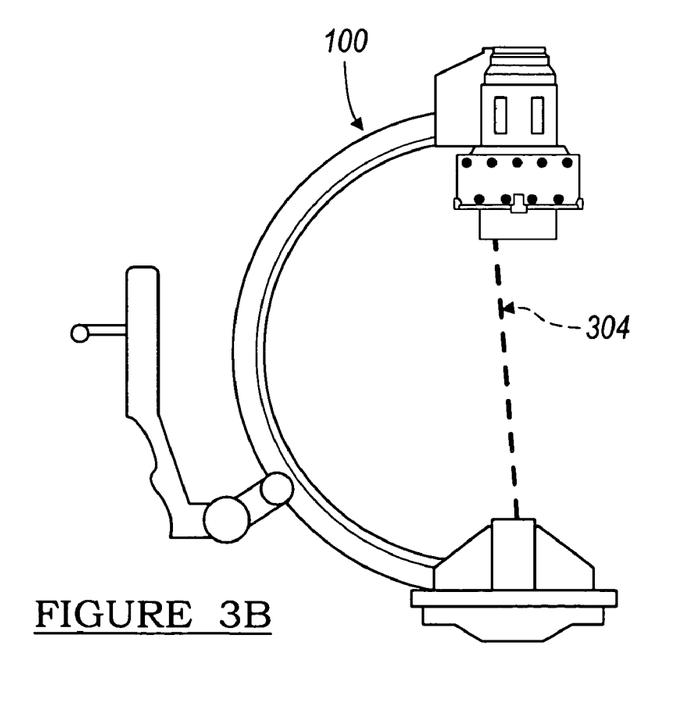

The image formation process in a system such as fluoroscopic C-arm imager 100 is governed by a geometric projective transformation which maps lines in the fluoroscope's field of view to points in the image (i.e., within the x-ray receiving section 105). This concept is illustrated in FIGS. 3A and 3B. Image 300 (and any image generated by the fluoroscope) is composed of discrete picture elements (pixels), an example of which is labeled as 302. Every pixel within image 300 has a corresponding three-dimensional line in the fluoroscope's field of view. For example, the line corresponding to pixel 302 is labeled as 304. The complete mapping between image pixels and corresponding lines governs projection of objects within the field of view into the image. The intensity value at pixel 302 is determined by the densities of the object elements (i.e., portions of a patient's anatomy, operating room table, etc.) intersected by the line 304. For the purposes of computer assisted navigational guidance, it is necessary to estimate the projective transformation which maps lines in the field of view to pixels in the image, and vice versa. Geometric projective transformation is well known in the art.

Intrinsic calibration, which is the process of correcting image distortion in a received image and establishing the projective transformation for that image, involves placing "calibration markers" in the path of the x-ray, where a calibration marker is an object opaque or semi-opaque to x-rays. Calibration markers 111 are rigidly arranged in predetermined patterns in one or more planes in the path of the x-rays and are visible in the recorded images. Tracking targets, such as emitters or reflectors 109, are fixed in a known position relative to calibration markers 111.

Because the true relative position of the calibration markers 111 in the recorded images are known, computer 120 is able to calculate an amount of distortion at each pixel in the image (where a pixel is a single point in the image). Accordingly, computer 120 can digitally compensate for the distortion in the image and generate a distortion-free, or at least a distortion improved image. Alternatively, distortion may be left in the image, and subsequent operations on the image, such as superimposing an iconic representation of a surgical instrument on the image (described in more detail below), may be distorted to match the image distortion determined by the calibration markers. The calibration markers can also be used to estimate the geometric perspective transformation, since the position of these markers are known with respect to the tracking target emitters or reflectors 109 and ultimately with respect to tracking sensor 130. A more detailed explanation of methods for performing intrinsic calibration is described in the references B. Schuele et al., "Correction of Image Intensifier Distortion for Three-Dimensional Reconstruction," presented at SPIE Medical Imaging 1995, San Diego, Calif., 1995 and G. Champleboux et al., "Accurate Calibration of Cameras and Range Imaging Sensors: the NPBS Method," Proceedings of the 1992 IEEE International Conference on Robotics and Automation, Nice, France, May 1992, and U.S. application Ser. No. 09/106,109, filed on Jun. 29, 1998 by the present assignee, the contents of which are hereby incorporated by reference.

Calibration and tracking target 106 may be attached to x-ray receiving section 105 of the C-arm. Alternately, the target 106 can be mechanically independent of the C-arm, in which case it should be positioned such that the included calibration markers 111 are visible in each fluoroscopic image to be used in navigational guidance. Element 106 serves two functions. The first, as described above, is holding calibration markers 111 used in intrinsic calibration. The second function, which is described in more detail below, is holding infrared emitters or reflectors 109, which act as a tracking target for tracking sensor 130.

Tracking sensor 130 is a real-time infrared tracking sensor linked to computer 120. Specially constructed surgical instruments and other markers in the field of tracking sensor 130 can be detected and located in three-dimensional space. For example, a surgical instrument 140, such as a drill, is embedded with infrared emitters or reflectors 141 on its handle. Tracking sensor 130 detects the presence and location of infrared emitters or reflectors 141. Because the relative spatial locations of the emitters or reflectors in instrument 140 are known a priori, tracking sensor 130 and computer 120 are able to locate instrument 140 in three-dimensional space using well known mathematical transformations. Instead of using infrared tracking sensor 130 and corresponding infrared emitters or reflectors, other types of positional location devices which are known in the art may be used. For example, positional location devices based on magnetic fields, sonic emissions, or radio waves are also within the scope of the present teachings.

Reference frame marker 150, like surgical instrument 140, is embedded with infrared emitters or reflectors, labeled 151. As with instrument 140, tracking sensor 130 similarly detects the spatial location of emitters/reflectors 151, through which tracking sensor 130 and computer 120 determine the three-dimensional position of dynamic reference frame marker 150. The determination of the three-dimensional position of an object relative to a patient is known in the art, and is discussed, for example, in the following references, each of which is hereby incorporated by reference: PCT Publication WO 96/11624 to Bucholz et al., published Apr. 25, 1996; U.S. Pat. No. 5,384,454 to Bucholz; U.S. Pat. No. 5,851,183 to Bucholz; and U.S. Pat. No. 5,871,445 to Bucholz.

During an operation, dynamic reference frame marker 150 is attached in a fixed position relative to the portion of the patient to be operated on. For example, when inserting a screw into the spine of patient 110, dynamic reference frame marker 150 may be physically attached to a portion of the spine of the patient. Because dynamic reference frame 150 is in a fixed position relative to the patient anatomy, and instrument 140 can be accurately located in three dimensional space relative to dynamic reference frame 150, instrument 140 can also be located relative to the patient's anatomy.

As discussed above, calibration and tracking target 106 also includes infrared emitters or reflectors 109 similar to those in instrument 140 or dynamic reference frame 150. Accordingly, tracking sensor 130 and computer 120 may determine the three-dimensional position of calibration target 106 relative to instrument 140 and/or dynamic reference frame 150 and thus the patient position.

In general, the imaging system assists physicians performing surgery by displaying real-time or pre-acquired images, such as fluoroscopic x-ray images, of the patient 110 on display 121. Representations of surgical instruments 140 are overlaid on pre-acquired fluoroscopic images of patient 110 based on the position of the instruments determined by tracking sensor 130. In this manner, the physician is able to see the location of the instrument relative to the patient's anatomy, without the need to acquire real-time fluoroscopic images, thereby greatly reducing radiation exposure to the patient and to the surgical team. "Pre-acquired," as used herein, is not intended to imply any required minimum duration between receipt of the x-ray signals and displaying the corresponding image. Momentarily storing the corresponding digital signal in computer memory while displaying the fluoroscopic image constitutes pre-acquiring the image.

Figure 4:
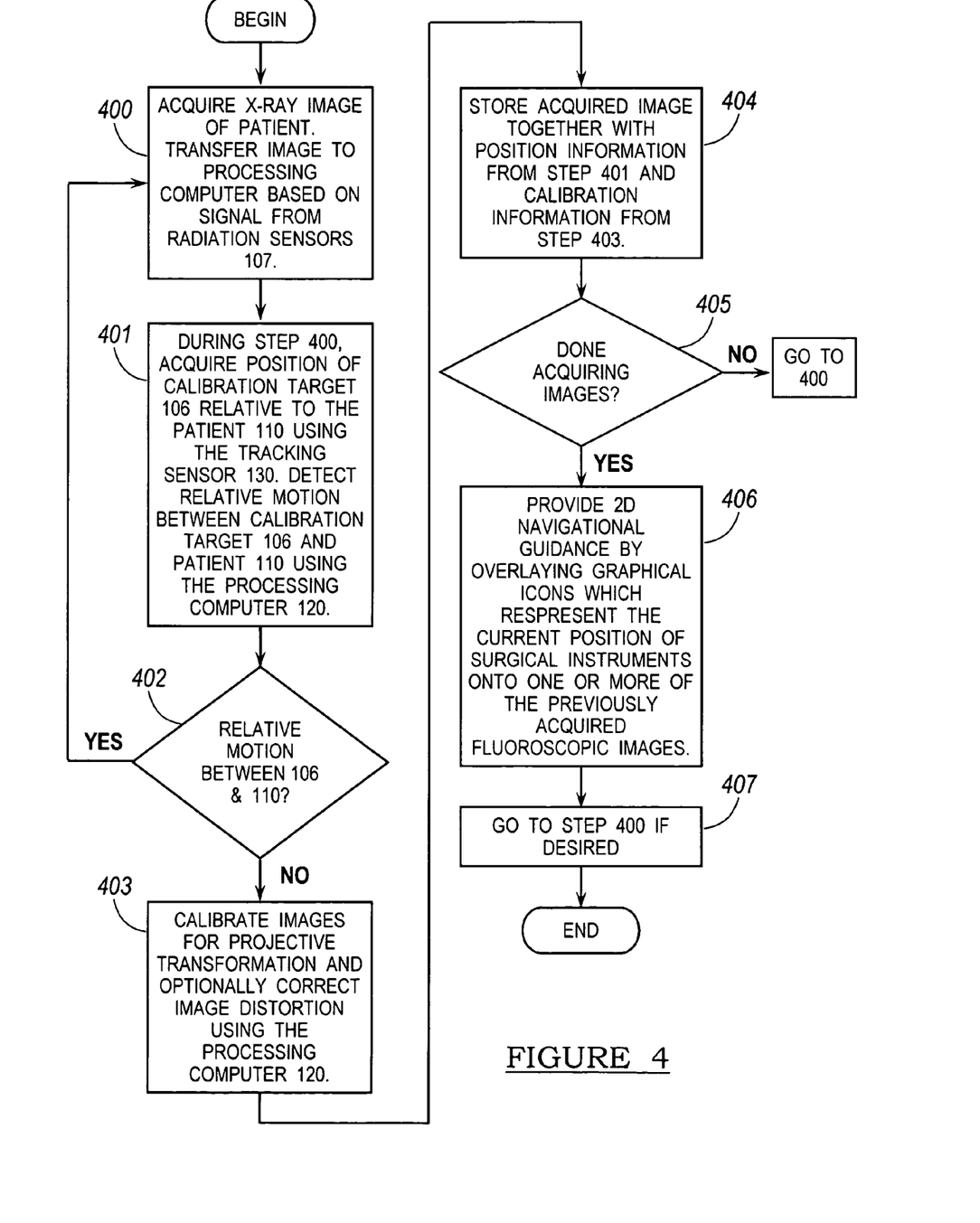
FIG. 4 is a flowchart depicting the operation of the surgical navigation system.

FIG. 4 is a flowchart depicting the operation of the surgical navigation system. The physician begins by acquiring one or more fluoroscopic x-ray images of patient 110 using imager 100 (step 400). As previously mentioned, acquiring an x-ray image triggers radiation sensors 107, which informs computer 120 of the beginning and end of the radiation cycle used to generate the image. For a fluoroscopic x-ray image acquired with imager 100 to be useable for navigational guidance, imager 100, when acquiring the image, should be stationary with respect to patient 110. If C-arm 103 or patient 110 is moving during image acquisition, the position of the fluoroscope will not be accurately determined relative to the patient's reference frame. Thus, it is important that the recorded position of imager 100 reflects the true position of the imager at the time of image acquisition. If imager 100 moves during the image acquisition process, or if imager 100 moves after image acquisition but before its position is recorded, the calibration will be erroneous, thereby resulting in incorrect graphical overlays. To prevent this type of erroneous image, computer 120 may examine the position information from tracking sensor 130 while radiation sensors 107 are signaling radiation detection. If the calibration and tracking target 106 moves relative to dynamic reference frame 150 during image acquisition, this image is marked as erroneous (Steps 401 and 402).

At the end of the radiation cycle, computer 120 retrieves the acquired image from C-arm control computer 115 and retrieves the location information of target marker 106 and dynamic reference frame 150 from tracking sensor 130. Computer 120 calibrates the acquired image, as described above, to learn its projective transformation and optionally to correct distortion in the image, (step 403), and then stores the image along with its positional information (step 404). The process of steps 400-404 is repeated for each image that is to be acquired (step 405).

Because the acquired images are stored with the positional information of the calibration and tracking target 106 and dynamic reference frame 150, the position of C-arm 103, x-ray source 104, and receiving section 105 for each image, relative to patient 110, can be computed based upon the projective transformation identified in the calibration process. During surgery, tracking sensor 130 and computer 120 detect the position of instrument 140 relative to dynamic reference frame 150, and hence relative to patient 110. With this information, computer 120 dynamically calculates, in real-time, the projection of instrument 140 into each fluoroscopic image as the instrument is moved by the physician. A graphical representation of instrument 140 may then be overlaid on the fluoroscopic images (step 406). The graphical representation of instrument 140 is an iconic representation of where the actual surgical instrument would appear within the acquired fluoroscopic x-ray image if imager 100 was continuously acquiring new images from the same view as the original image. There is no theoretical limit to the number of fluoroscopic images on which the graphical representations of instrument 140 may be simultaneously overlaid.

Figure 5A:
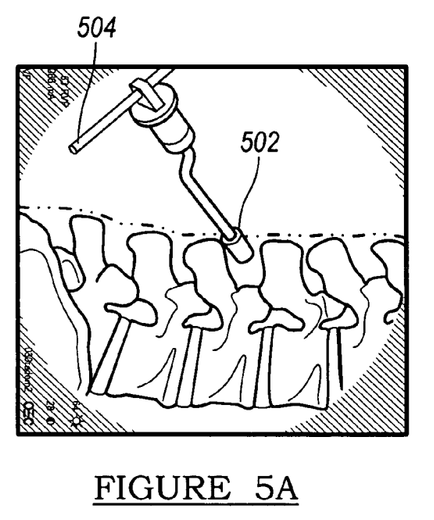
FIGS. 5A and 5B illustrate graphical representations of the surgical instrument superimposed onto a two-dimensional image of the patient.
Figure 5B:
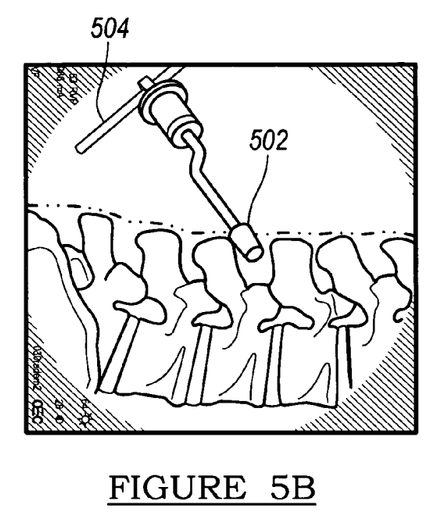

The graphical representation of the surgical instrument is a three-dimensional object superimposed onto a two-dimensional image of the patient. The three-dimensional representation of the instrument may appear to be directed into or out of the two-dimensional image as shown in FIGS. 5A and 5B. In FIG. 5A, the tip 502 of the instrument 504 and the projected length appear to be directed into the image. Conversely, in FIG. 5B, the tip 502 of the instrument 504 and the projected length appear to be coming out of the image.

When an image is acquired, it is acquired from a certain perspective or point-of-view. In the case of a C-arm imaging device 100, the perspective is determined by the orientation of the C-arm 103 around the patient 110. Specifically, the perspective is along the line connecting the image source 104 and the image receiver section 105. If the surgeon navigates the surgical instrument from the position of the image receiver section 105, the perspective of the virtual representation of the instrument will match the surgeon's perspective of the actual instrument. However, if the surgeon navigates from the position of the image source 104, the perspective of the virtual representation of the instrument will appear "flipped" from the surgeon's perspective of the actual instrument.

In accordance with the present teachings, the surgical instrument navigation system described above has been enhanced to allow a surgeon to invert the graphical representation of the instrument to match their perspective of the actual instrument. In various embodiments, the navigation system provides two possible perspectives: positive (+) or negative (−). The positive state renders the instrument from the perspective of the image receiver section 105; whereas the negative state renders the instrument from the perspective of the image source 104. It is envisioned that either state may be designated the default state. It is further envisioned that more than two perspectives may be available for selection by the surgeon.

Figure 6:
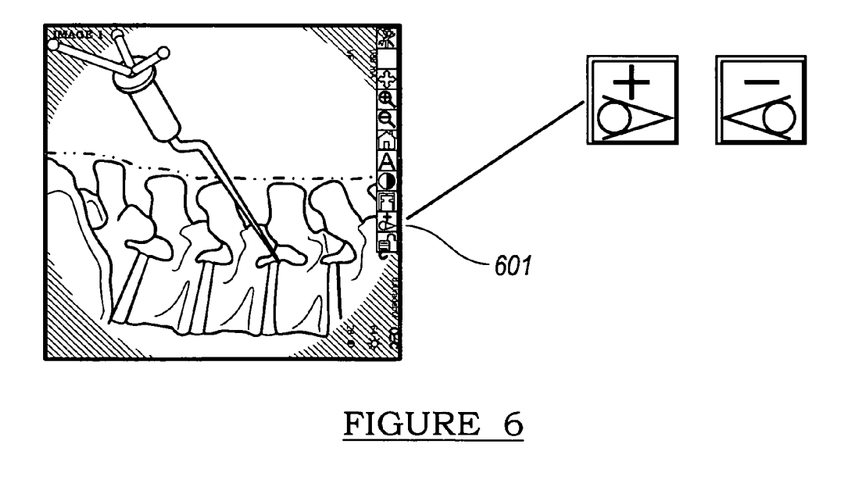
FIG. 6 illustrates an exemplary graphical user interface of the surgical instrument navigation system.

Referring to FIG. 6, the perspective of the instrument is selectable using a touch screen operable button 601 provided on the graphical user interface of the navigation system. One skilled in the art will readily recognize that rendering a particular perspective of the instrument does not affect the profile of the instrument or the location of the instrument on the image. The perspective selection only affects the internal contours that give the instrument the appearance into or out of the image as shown in FIGS. 5A and 5B. Although a touch screen operable button is possible, it is envisioned that other techniques for selecting the perspective of the instrument, such as a foot pedal or other switching device in close proximity to the surgeon, are also within the scope of the present teachings.

Figure 7:
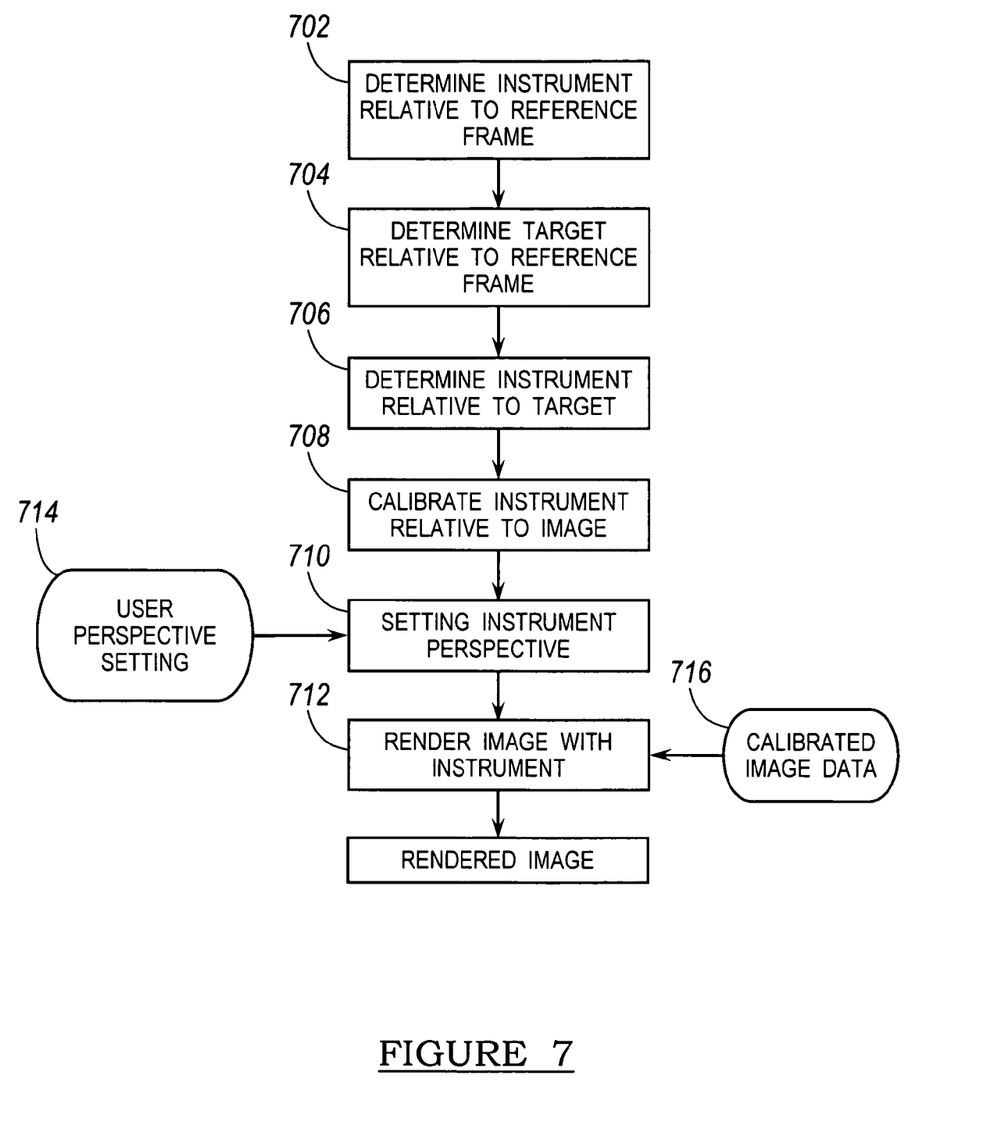
FIG. 7 is a flowchart depicting how perspective inversion is incorporated into the operation of the surgical instrument navigation system in accordance with the present teachings.

A more detailed description of how perspective inversion is incorporated into the operation of the surgical instrument navigation system is provided in conjunction with FIG. 7. As noted above, the projection of the instrument into the fluoroscopic image is calculated in real-time as the instrument is moved by the surgeon.

To do so, the tracking sensor 130, in conjunction with the computer 120, detects the position of the instrument 140 at step 702 relative to the dynamic reference frame 150, and thus relative to the patient 110. The tracking sensor 130, in conjunction with the computer 120, also determines the position of the tracking target 106 at step 704 relative to the dynamic reference frame 150. Based this position data, the computer 120 can determine the position of the instrument 140 relative to the tracking target 106 at step 706, and calibrate the position of the instrument relative to the image plane of the fluoroscopic images at step 708.

Prior to rendering the image, the navigation system accounts for the various user settings 714, including instrument perspective. The selected perspective setting 714 is input into the computer 120 at step 710 which in turn provides corresponding input to the graphic rendering software. One skilled in the art will readily recognize that other user settings (e.g., zoom, rotate, ect.) may be accounted for by the navigation system.

Lastly, the fluoroscopic image is rendered by the navigation system at step 712. Specifically, the three-dimensional representation of the surgical instrument is rendered from the perspective input by an operator of the navigation system. The representation of the instrument is then superimposed over the previously calibrated image data for the patient. In this way, the perspective of the displayed instrument matches the surgeon's perspective of the actual instrument. As noted above, the representation of the surgical instrument is tracked in real-time as it is moved by the surgeon.

While the teachings have been described according to various embodiments, it will be understood that the teachings are capable of modification without departing from the spirit of the teachings as set forth in the appended claims.

What is claimed is:

1. A surgical instrument navigation system operable to track a position of a surgical instrument relative to a patient space, comprising:
   a tracking subsystem operable to capture real-time position data indicative of the position of the surgical instrument; and
   a processor adapted to access image data representative of the patient space in a selected orientation and to process the image data and the position data from the tracking subsystem, the processor operable to generate a three-dimensional representation of the surgical instrument as it would visually appear from either of at least two different perspectives and to overlay the representation of the surgical instrument onto the image data of the patient.

2. The surgical instrument navigation system of claim 1, further comprising:
   a display in communication with the processor, the display operable to display the representation of the surgical instrument in at least one of the two different perspectives superimposed onto the image data of the patient in the first orientation.

3. The surgical instrument navigation system of claim 1, wherein the display includes at least one of an overhead display, a monitor, a heads-up display, or combinations thereof.

4. The surgical instrument navigation system of claim 1, further comprising:
   a surgical instrument operable to be moved relative to the patient space.

5. The surgical instrument navigation system of claim 4 wherein the processor is further operable to track in real-time the position of the surgical instrument as it is moved by a surgeon and generate a corresponding representation of the surgical instrument in relation to the image data of the patient.

6. The surgical instrument navigation system of claim 1, further comprising:
   a rotatable C-arm operable to provide the image data;
   wherein at least one of the two different perspectives is determined by an orientation of the C-arm relative to the patient.

7. The surgical instrument navigation system of claim 1 further comprising:
   an imaging device that includes an image source emanating radiation towards the patient and an image receiver positioned to receive radiation from the image source, such that the generated representation of the surgical instrument visually appears as it would from either the perspective of the image source or the perspective of the image receiver.

8. The surgical instrument navigation system of claim 1 wherein the generated representation of the surgical instrument visually appears from a perspective that is selectable by a user of the navigation system.

9. The surgical instrument navigation system of claim 2 wherein the display further includes a touch screen activated button operable to select the perspective of the generated representation of the surgical instrument.

10. The surgical instrument navigation system of claim 2 wherein the display visually indicates the perspective of the generated representation of the surgical instrument as it appears to a user of the navigation system.

11. The surgical instrument navigation system of claim 1 further comprising at least one of an x-ray imaging device, an isocentric C-arm imaging device, computed tomography imaging device, magnetic resonance imaging device, a two-dimensional imaging device, a three-dimensional imaging device, or combinations thereof.

12. The surgical instrument navigation system of claim 1 wherein the tracking subsystem employs a non-contact positional location technique that is based on at least one of radio waves, infrared energy, magnetic fields, sonic emissions, or combinations thereof.

13. A surgical instrument navigation system for assisting in tracking a surgical instrument in relation to a patient space, comprising:
   a surgical instrument an imaging subsystem operable to produce image data representative of the patient space produced in relation to an image receiver and a transmitter;

a tracking subsystem operable to capture in real-time position data indicative of a position of the surgical instrument;

a processor operable to process the image data and the position data from the tracking subsystem, the processor operable to generate a three-dimensional representation of the surgical instrument as it would visually appear from either the perspective of the transmitter or the perspective of the image receiver and to overlay the representation of the surgical instrument onto the image data of the patient in the orientation.

14. The surgical instrument navigation system of claim 13, further comprising:

a display in communication with the processor, the display operable to display the representation of the surgical instrument superimposed onto the image data of the patient.

15. The surgical instrument navigation system of claim 13 wherein the processor is further operable to track in real-time the position of the surgical instrument as it is moved by a surgeon and generate a corresponding representation of the surgical instrument in relation to the image data of the patient.

16. The surgical instrument navigation system of claim 13 wherein the generated representation of the surgical instrument visually appears from a perspective that is selectable by a user of the navigation system.

17. The surgical instrument navigation system of claim 14 wherein the display is further defined as a graphical user interface having a touch screen activated button to select the perspective of the generated representation of the surgical instrument.

18. The surgical instrument navigation system of claim 13 wherein the imaging subsystem includes at least one of an x-ray imaging device, computed tomography imaging device, magnetic resonance imaging device, isocentric C-arm imaging device, a three-dimensional imaging device, a two-dimensional imaging device, or combinations thereof.

19. The surgical instrument navigation system of claim 13 wherein the tracking subsystem employs a non-contact positional location technique that is based on at least one of radio energy, infrared waves, magnetic fields, sonic emissions, or combinations thereof.

* * * * *

UNITED STATES PATENT AND TRADEMARK OFFICE
CERTIFICATE OF CORRECTION

PATENT NO. : 7,630,753 B2
APPLICATION NO. : 11/188972
DATED : December 8, 2009
INVENTOR(S) : Simon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 966 days.

Signed and Sealed this

Second Day of November, 2010

David J. Kappos
*Director of the United States Patent and Trademark Office*